United States Patent
Lesic

(10) Patent No.: US 10,654,075 B2
(45) Date of Patent: May 19, 2020

(54) APPARATUS AND METHODS FOR TREATING A MEDICAL DEVICE AND HAND DISINFECTION

(71) Applicant: Zoran Lesic, Denver, CO (US)

(72) Inventor: Zoran Lesic, Denver, CO (US)

(*) Notice: Subject to any disclaimer, the term of this patent is extended or adjusted under 35 U.S.C. 154(b) by 1515 days.

(21) Appl. No.: 14/540,115

(22) Filed: Nov. 13, 2014

(65) Prior Publication Data

US 2015/0128997 A1    May 14, 2015

Related U.S. Application Data

(60) Provisional application No. 61/903,674, filed on Nov. 13, 2013.

(51) Int. Cl.
| | |
|---|---|
| *B08B 1/00* | (2006.01) |
| *A61B 7/00* | (2006.01) |
| *A61B 90/80* | (2016.01) |
| *A61B 90/70* | (2016.01) |

(52) U.S. Cl.
CPC ............. *B08B 1/006* (2013.01); *A61B 7/00* (2013.01); *A61B 90/70* (2016.02); *A61B 90/80* (2016.02); *B08B 1/00* (2013.01); *B08B 1/008* (2013.01)

(58) Field of Classification Search
CPC .. B08B 1/04; B08B 1/00; B08B 1/006; B08B 11/02; B08B 9/42; A47L 11/4047
USPC ........................................................ 15/97.1
See application file for complete search history.

(56) References Cited

U.S. PATENT DOCUMENTS

| | | | |
|---|---|---|---|
| 4,280,244 A * | 7/1981 | Spirig | A47L 23/263 |
| | | | 15/36 |
| 4,354,292 A | 10/1982 | Telestad et al. | |
| 5,132,518 A | 7/1992 | Solacoff | |
| 5,641,464 A | 6/1997 | Briggs, III et al. | |
| 6,018,835 A * | 2/2000 | Schonfeld | B08B 1/008 |
| | | | 134/198 |
| 7,360,625 B2 | 4/2008 | Stickley | |
| 7,503,335 B2 | 3/2009 | Perlman et al. | |
| 7,705,325 B2 | 4/2010 | Vestal | |
| 7,807,102 B1 | 10/2010 | Rezaizadeh et al. | |
| 8,083,998 B2 | 12/2011 | Hurwitz et al. | |
| 8,393,818 B2 | 3/2013 | Perlman et al. | |

(Continued)

FOREIGN PATENT DOCUMENTS

| | | |
|---|---|---|
| CA | 2440636 | 9/2002 |
| WO | WO 2010/131253 | 11/2010 |

(Continued)

OTHER PUBLICATIONS

International Search Report and Written Opinion for International Patent Application No. PCT/US14/65339, dated Feb. 13, 2015, 9 pages.

(Continued)

*Primary Examiner* — Shay Karls
(74) *Attorney, Agent, or Firm* — FisherBroyles, LLP; Ian Walsworth

(57) ABSTRACT

A cleaning device and methods for cleaning medical devices, in particular, stethoscopes, is provided. In one aspect, the cleaning device includes a housing defining an interior chamber and configured to mount a wipe device, the housing including an aperture configured to receive a medical device, and a wipe device mounted within the interior chamber and including at least two rollers.

10 Claims, 8 Drawing Sheets

(56) References Cited

U.S. PATENT DOCUMENTS

2003/0170453 A1* 9/2003 Foss ................. A01N 57/16
428/373
2006/0237475 A1 10/2006 Agarwal
2008/0087560 A1 4/2008 Kelly

FOREIGN PATENT DOCUMENTS

| WO | WO 2011/060132 | 5/2011 |
| WO | WO 2012/010902 | 1/2012 |
| WO | WO 2012/141549 | 10/2012 |

OTHER PUBLICATIONS

Garmage, "A guide to selection and use of disinfectants," BC Centre for Disease Control, 2003, 18 pages.

* cited by examiner

THESE DRAWINGS TO SCALE
ALL DIMENSIONS IN CM

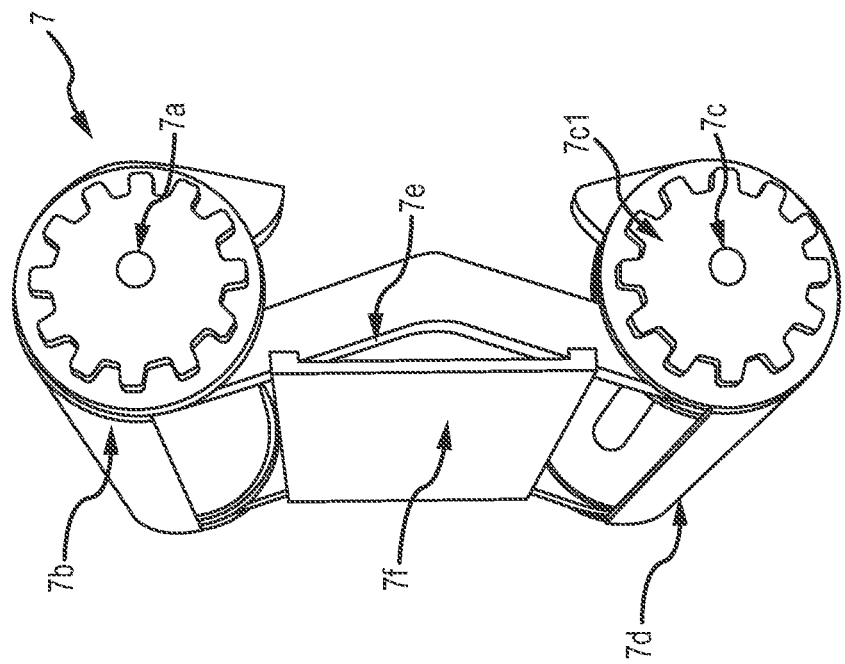
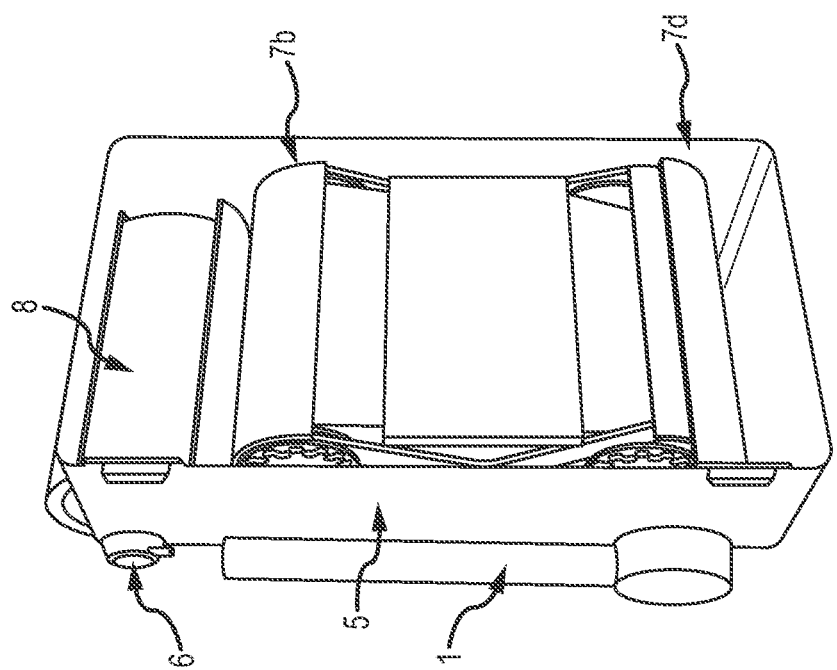

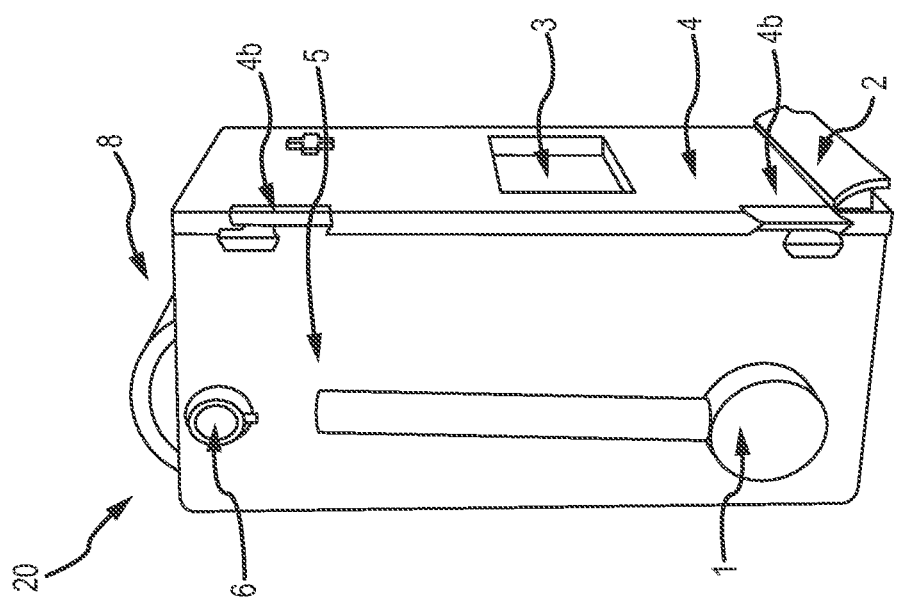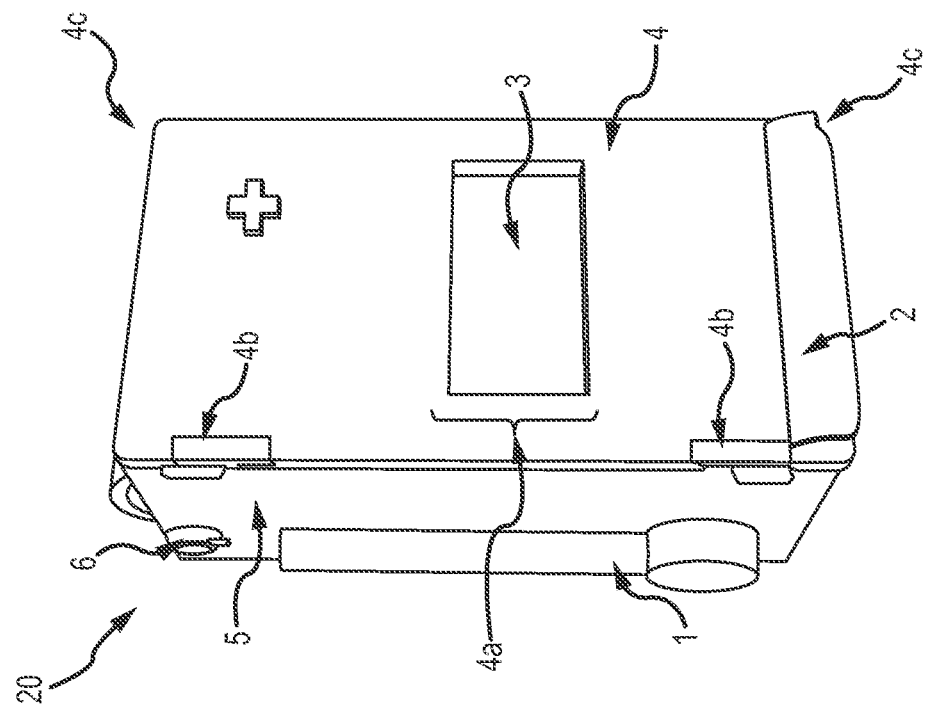

APPARATUS AND METHODS FOR TREATING A MEDICAL DEVICE AND HAND DISINFECTION

CROSS REFERENCE TO RELATED APPLICATION

The present application claims the benefit of U.S. Provisional Application Ser. No. 61/903,674, filed Nov. 13, 2013, entitled "APPARATUS AND METHODS FOR TREATING A MEDICAL DEVICE AND HAND DISINFECTION," which is incorporated herein by this reference in its entirety.

TECHNICAL FIELD

The present invention generally relates to medical instruments and, more specifically, to an apparatus and methods for cleaning medical devices, in particular, stethoscopes.

BACKGROUND

Healthcare-associated infections are infections that patients acquire during the course of receiving healthcare treatment for other conditions. They are a significant hazard for patients, and health care workers are potential sources of these infections which are a significant cause of morbidity, mortality, and increased cost. Reported incidence of these infections is as high as 15.5% of hospitalized patients in some series. Hospital environment likely acts as a reservoir for the potential pathogens. The natural history of the development of hospital-acquired infections appears to begin with exposure of patients to pathogenic bacteria which have colonized hospital equipment, or skin and nasopharynx of hospital personnel. Subsequently, colonization of the patients' skin, gut, or systems with hospital flora occurs; infections ensue when the normal body defenses are impaired through underlying diseases, administration of immunomodulating therapy or use of invasive devices.

While many of the pathogens can be transmitted by hand carriage, there are mechanisms in place to address this issue, such as hospital-wide incentives reminding health care workers to wash hands before and after seeing each patient, or conveniently available hand sanitizers in each patient room which make it easy to minimize these transmissions. However, transmission of infections through contaminated medical devices such as stethoscopes has also been demonstrated, and studies show that they can harbor various organisms on their diaphragm surfaces. Following contact with infected skin, pathogens can attach and establish themselves on the diaphragms of stethoscopes and subsequently be transmitted to other patients during routine physical examination.

Contaminants that have been well documented on stethoscope surfaces include coagulase negative staphylococci, *Staphylococcus aureus, Corynebacterium* spp., *Bacillus* spp., *Neisseria* spp., alpha-hemolytic streptococci, *Micrococcus luteus, Enterococcus* spp., *Candida* spp., Gram negative organisms (including *Pseudomonas aureginosa*; also non-fermenting gram negative bacilli, including *Acinetobacter* spp. and *Stenotrophomanas maltophilia*, both of which are of increasing importance as causes of multi-drug resistant infections in immune-compromised hospital patients), *Enterococcus faecalis, Escherichia coli* and *Aspergillus* spp. Point-prevalence culture surveys have also demonstrated that stethoscope diaphragms may be contaminated with pathogens such as *Clostridium difficile*. Also, it is known that several common viruses (e.g. enteroviruses and small round structured viruses) survive well in the environment and may be transmitted by fomites on stethoscope surfaces. Norovirus has been shown on hospital surfaces as well and could likely be transmitted via stethoscopes.

In addition to a wide variety of organisms that have been shown to contaminate stethoscope surfaces, the sheer prevalence of such contamination is stunning; at least one organism has been demonstrated in 79% to 100% of stethoscope surfaces surveyed in various series.

The hands of healthcare workers may well represent the final mode of transmission as it appears that sites frequently touched by hands are thought to provide the greatest risk for patients. For example, there seems to be a link between *Staphylococcus aureus* nasal carriage and staphylococcal infection; a causal relation between carriage and an infecting strain is shown by the fact that the nasal strain of *Staphylococcus aureus* and the infecting strain share the same genotype. Given the propensity for people to pick, touch, or blow their noses, it is not surprising that carriers will often harbor their own strain of *Staphylococcus aureus* on their fingers, which they will then transfer to any site accessible to their hands. This likely applies to transmission of pathogens from all the surfaces that health care workers touch on a routine basis, including contaminants among different patients. We may think then that maintaining good hand hygiene is enough to prevent these hospital-acquired infections. However, even exemplary hand hygiene cannot be expected to break the chain of infection when the environment is heavily contaminated. If a health care worker uses wall-mounted hand disinfectant prior to and after each patient contact but they do not disinfect their stethoscope routinely, then their clean hands will become contaminated from touching the dirty stethoscopes again and will potentially contaminate the patients anyway. It follows that anything that depends on hands for functionality is at risk of contamination from a carrier's strain, even if hands are disinfected. As even short periods of contact between a patient's skin and the stethoscope can result in transfer of bacteria, there is a need for strategies to decrease bacterial contamination of stethoscopes and strict adherence to stethoscope disinfection practices by health workers will minimize cross-contamination and ensure improved patient safety in hospitals.

An obvious risk of lack of stethoscope disinfection practices is dissemination of multi-resistant organisms. There are increasing reports of these organisms being transmitted via stethoscope surfaces, capable of initiating severe infections in a hospital environment, which may require contact isolation. Patients with open wounds, such as those with burns or tracheotomies, may be colonized leading to infection at a later time.

Multiple studies demonstrated that enhanced cleaning of clinical equipment and other inanimate near-patient sites is an effective mechanism of reducing MRSA, *Clostridium difficile*, and Norovirus infections. Specifically, cleaning the stethoscope diaphragm has been shown to result in immediate reduction of bacterial contamination on its surface. In order to be effective, decontamination would have to be performed after each use of the stethoscope. Unfortunately, despite this wide array of pathogenic organisms that could be spread among patients and evidence that disinfection may decrease contamination, studies show that routine disinfection of stethoscopes in between patients and before each patient contact is not an established practice and according to some studies it is hardly ever undertaken. Multiple studies confirm that surveyed physicians and other health care professionals rarely clean their stethoscopes on a regular basis. In one series, 40% of health care workers studied did not clean their stethoscopes at all, while among the ones who did, frequency of cleaning was only monthly to yearly. The same studies report lack of guidelines or advise being given to personnel on how or how regularly to disinfect stethoscopes. As low as 0-3% of health-care providers clean their stethoscopes regularly in other series, and just 10% cleaned them when they were soiled with blood or human secretions.

The importance of routine disinfection of stethoscopes before each and every patient contact cannot be emphasized enough. A study that examined transfer of organisms from patients to stethoscope surfaces in a series of patients demonstrated than when a sterilized stethoscope (as evidenced by negative culture of the diaphragm after disinfection) is applied to only one patient's chest, in 57% of cases stethoscopes grew *Staphylococcus aureus*. There is a statistically significant correlation between the mean number of staphylococcal CFUs (colony forming units) grown from stethoscope surfaces and periods of time in between cleanings—specifically, there is a marked increased in mean CFUs as the stethoscopes went for longer periods of time in between cleanings. The highest levels of bacterial contamination were found on stethoscopes that had never been cleaned.

Strict adherence to stethoscope disinfection practices by health workers can minimize cross-contamination and ensure improved patient safety in hospital environment. Studies support the necessity for clear disinfecting guidelines, outlining the need to disinfect stethoscopes before and after every patient contact in order to limit the bacterial load to which patients are exposed. However, currently available methods involving alcohol or bleach wipes are cumbersome, time consuming, and inconvenient; many times, alcohol wipes are not even available immediately upon entrance to a patient's room. These factors likely account for such a low compliance rates, given that convenience and availability appear to determine the method of stethoscope disinfection used by health care professionals.

Strategies to minimize the transmission of infection from stethoscopes have been proposed, including the use of disposable stethoscopes, especially for clinical high-risk environments, and the use of a single-use, membrane cover over the stethoscope head to create a prophylactic barrier. Although these strategies could minimize the risk of stethoscope transmission of infections, they are unlikely to be cost-effective in developing countries, and even in developed countries where they can be easily obtained, they remain cumbersome and inconvenient, adding more steps for healthcare workers to follow, in turn resulting in lower rates of compliance.

Numerous portable stethoscopes cleaning devices exist. For example, Cleanstethoscope by Cleanint offers a stethoscope cleaning device comprising a holder for an insertable sponge-like insert. The insert comprises a proprietary, alcohol-free cleaning solution. When not in use, the care-provider places the diaphragm into the holder where it is in contact with the sponge and the cleaning solution.

Although, small and compact, this device has several potential limitations and disadvantages. For example, germs and spores that are removed from the diaphragm surface will remain in the sponge, and may potentially be reintroduced onto the stethoscope during the next use and transmitted to subsequent patients. In addition, this device requires the user to carry replacement sponges, making the system potentially inconvenient, resulting in the care-provider being less likely to replace them with the frequency needed for the system to be most effective. Also, a care-provider needs to touch the product with their hands, to place the sponges in the holder. Also, if the user does not pay close attention to the freshness of the sponge, they may end up using the dry sponge many times over before it is replaced with a fresh one, causing even more contamination than not using it at all. So, unless gloves are strictly worn 100% of the time when using the stethoscope and when replacing sponges, contamination may result. Since, it is suggested that his system be worn on a care-giver's lab coat, the lab coat itself may become contaminated as a result of using of the device.

U.S. Pat. No. 7,360,625 to Stickley ("Stickley") discloses another stethoscope sanitizing device that is connected directly to the stethoscope. When the stethoscope is not being used, the device covers the diaphragm and bell portions with sanitizing pads. When the care-giver wishes to use the stethoscope, the device is slid up a length of the stethoscope to expose the diaphragm for use. This device appears to have some of the same potential disadvantages as the Cleanstethoscope device, including the accumulation of contamination in the cleaning device itself over time, and accidental contamination of other parts of the stethoscope as well as the care-giver's clothing. Also, carrying extra weight is likely to result in discomfort for the provider, which would likely lead to poor compliance. Another device with similar features and disadvantages is disclosed in PCT Patent Application Publication No. WO 2010/131253 to Nahman et al. ("Nahman"). Stickley and Nahman are incorporated by reference in their entirety for all purposes.

U.S. Pat. No. 7,705,325 to Vestal ("Vestal") discloses a stethoscope sterilization device, also mounted on the stethoscope itself. In this case the device comprises a cover member and an ultraviolet light source. The ultraviolet (UV) light source is operably engaged with the cover member and configured to emit ultraviolet radiation for interacting with the face portion of the stethoscope only when the cover member is covering the stethoscope's face portion. However, there are potential disadvantages to this system, too. Even though studies demonstrate that UV light can be effective in disinfecting surfaces, this is typically done in controlled laboratory environment, using high power UV light for long periods of time, which do not necessarily replicate the "in-use" conditions. In addition, the presence of organic matter on surfaces reduces the efficacy of UV radiation in killing *C. difficile* spores, necessitating the combined use of some mechanical cleaning means for removing the organic matter, film, or coating. Again, this type of system leads to the issue of extra weight that needs to be carried around by the care-giver. Vestal is incorporated by reference in entirety for all purposes.

Canadian Patent No. 2,440,636 to Giroux et al. ("Giroux") discloses a protective sleeve cartridge that is located on the stethoscope head itself. The cartridge contains a plurality of longitudinally connected sleeves, separated by perforations. With each use, the care-giver uses a new sleeve to cover the stethoscope diaphragm, thus avoiding direct contact with the patient's skin. Once finished with the examination, the care-giver discards the used sleeve, and covers the stethoscope with a new one. This system also has some potential disadvantages. First, although this system may minimize contact of the stethoscope with the patient, it does nothing to actually clean and/or disinfect the stethoscope. In addition, attaching this system to the stethoscope appears to require some dexterity to properly cover the stethoscope. Finally, accidental contamination of the sleeve seems likely, which in turn, can lead to subsequent accidental contamination. Giroux is incorporated by reference in entirety for all purposes.

Therefore, and in light of CDC statistics that show that 1 in 20 hospitalized patients will contract a hospital-acquired infection, and considering the fact that the annual cost of hospital-acquired infections in the US ranges up to $45 billion according to some estimates, there is a clear need for improved devices and methods for cleaning stethoscopes, in addition to cleaning other commonly used medical devices that are placed in contact with a patient's skin, to prevent or reduce the frequency of hospital-acquired infections.

SUMMARY

It is therefore an objective of this disclosure to provide an improved device for cleaning, sterilizing, and/or disinfecting commonly used, hand-held medical devices, in particular stethoscopes. It is one objective of the present invention, to provide a cleaning device that provides a mechanical means, including contact with an abrasive surface, for cleaning a medical device. It is a further objective of this disclosure, to provide a cleaning device that minimizes accidental contamination by only utilizing a cleaning surface, sheet, or belt a single time; e.g. once a cleaning surface is used to clean a device, it is disposed of and is not recycled for future subsequent cleaning. It is a further objective to provide a medical device cleaning apparatus or system that utilizes a non-liquid, disposable cartridge cleaning system.

In one embodiment, a cleaning device to clean a medical device is disclosed, the cleaning device comprising: a housing defining an interior chamber and configured to receive a wipe device, the housing comprising an aperture configured to receive the medical device; and a wipe device comprising at least a first roller, a second roller, and a plurality of cleaning wipes, the plurality of cleaning wipes operatively engaged with the first roller and the second roller; wherein the medical device is positioned at least one of within and through the aperture to engage the cleaning wipe.

In another embodiment, a cleaning device to clean a medical device is disclosed, the cleaning device comprising: a housing defining an interior chamber and configured to mount a wipe device, the housing comprising an aperture configured to receive the medical device; and a disposable wipe device mounted within the interior chamber and comprising at least a first roller, a second roller, a surface support and a plurality of cleaning wipes, the plurality of cleaning wipes operatively engaged with the first roller and the second roller; a mechanism to advance the plurality of cleaning wipes, the mechanism configured to advance the plurality of cleaning wipes from the first roller to the second roller; wherein the plurality of cleaning wipes are wound around at least one of the first roller and the second roller, and are configured to unwind from the first roller onto the second roller when the plurality of cleaning wipes advance from the first roller to the second roller; wherein the plurality of cleaning wipes comprise a first cleaning wipe and a second cleaning wipe, wherein the mechanism advances the first cleaning wipe from a position adjacent the aperture to a position toward the second roller and advances the second cleaning wipe to a position adjacent the aperture; wherein the medical device is positioned at least one of within and through the aperture to engage the cleaning wipe.

In yet another embodiment, a method of cleaning a medical device is disclosed, the method comprising: providing a cleaning device comprising a housing defining an interior chamber and configured to mount a wipe device, the housing comprising an aperture configured to receive the medical device; and a wipe device mounted within the interior chamber and comprising at least a first roller, a second roller, and a plurality of cleaning wipes, the plurality of cleaning wipes operatively engaged with the first roller and the second roller; wherein the medical device is positioned at least one of within and through the aperture to engage the cleaning wipe; positioning a medical device within the aperture so as to engage a cleaning wipe; and holding the medical device against the cleaning device while the wipe device advances a cleaning wipe.

The preceding is a simplified summary to provide an initial understanding of the aspects, embodiments and configurations disclosed herein. This summary is neither an extensive nor exhaustive overview of the aspects, embodiments, or configurations. It is intended neither to identify key or critical elements, nor to delineate the scope of the aspects, embodiments, or configurations but to present selected concepts in a simplified form as an introduction to the more detailed description presented below. As will be appreciated, other aspects, embodiments, and configurations are possible utilizing, alone or in combination, one or more of the features set forth above or described in detail below.

BRIEF DESCRIPTION OF DRAWINGS

The accompanying drawings are incorporated into and form a part of the specification to illustrate examples of how the aspects, embodiments, or configurations can be made and used and are not to be construed as limiting the aspects, embodiments, or configurations to only the illustrated and described examples. Further features and advantages will become apparent from the following, more detailed, description of the various aspects, embodiments, or configurations.

FIG. 3A is a cut-away left front perspective view of the embodiment of a cleaning device of FIG. 1A;

FIG. 3B is a left front perspective view of the wipe device element of the embodiment of a cleaning device of FIG. 3A;

FIG. 4A is a left front perspective view of the embodiment of a cleaning device of FIG. 1A;

FIG. 4B is an additional left front perspective view of the embodiment of a cleaning device of FIG. 4A;

Figure 1A:
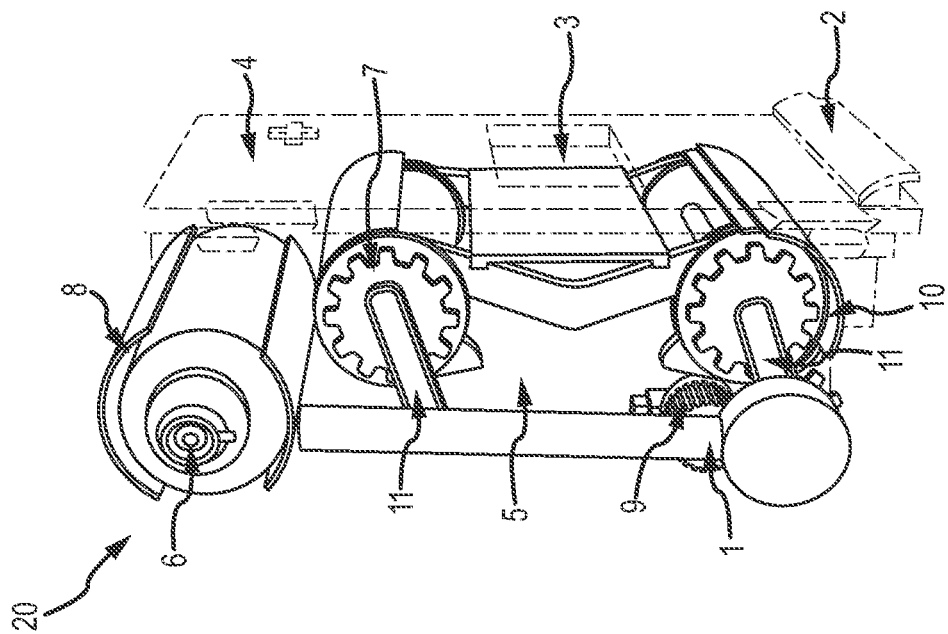
FIG. 1A is a cut-away left front perspective view of one embodiment of a cleaning device.
Figure 1B:
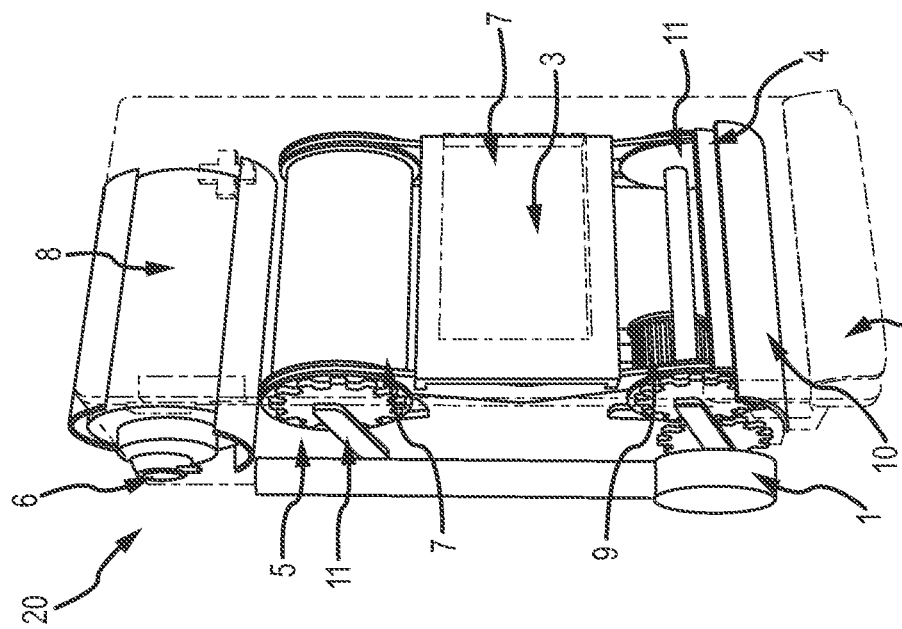
FIG. 1B is another cut-away left front perspective view of the embodiment of a cleaning device of FIG. 1A.
Figure 2C:
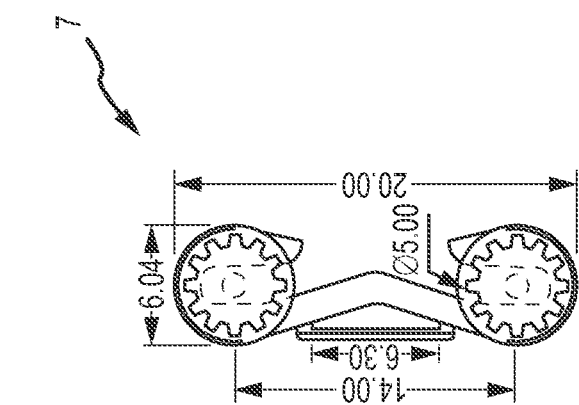
FIG. 2C is a left side view of the wipe device element of the embodiment of a cleaning device of FIG. 2A (this drawing is to scale)
Figure 2B:
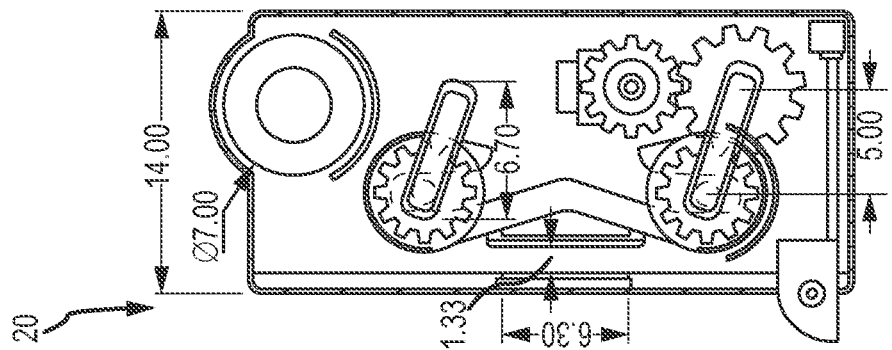
FIG. 2B is a left side cut-away view of the embodiment of a cleaning device of FIG. 2A (this drawing is to scale)
Figure 2A:
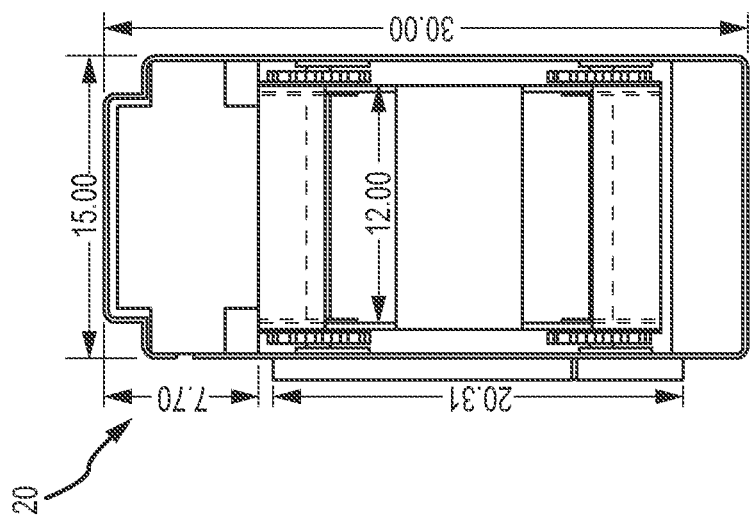
FIG. 2A is a rear cut-away view of the embodiment of a cleaning device of FIG. 1A (this drawing is to scale)
Figure 3D:
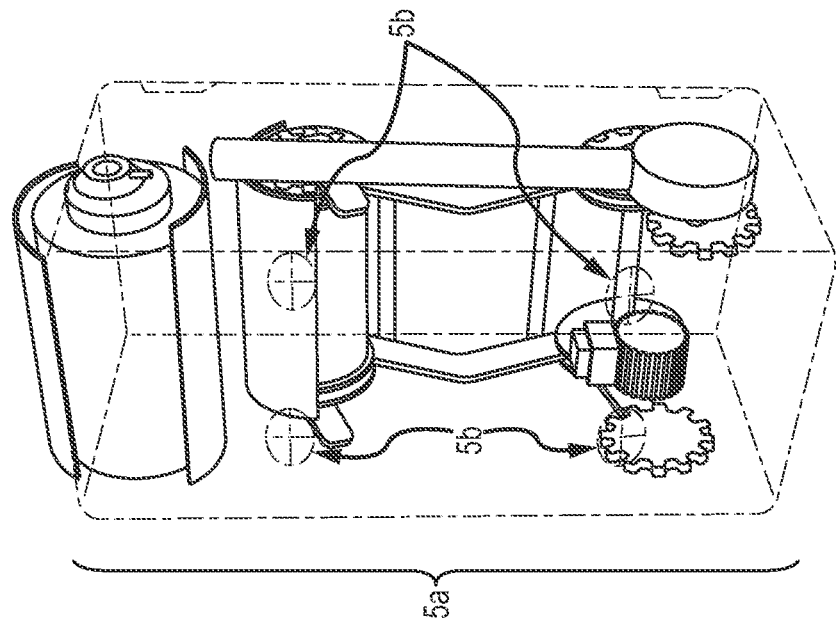
FIG. 3D is a partial cut-away front left perspective view of the embodiment of a cleaning device of FIG. 3A.
Figure 3C:
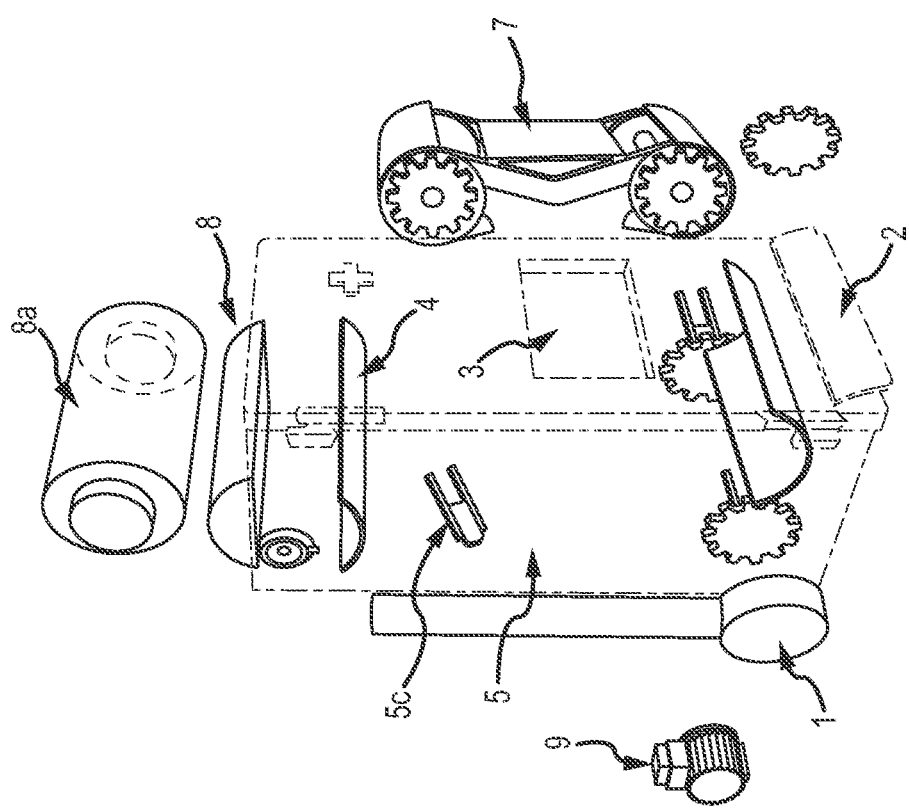
FIG. 3C is an exploded view of the embodiment of a cleaning device of FIG. 3A.
Figure 3E:
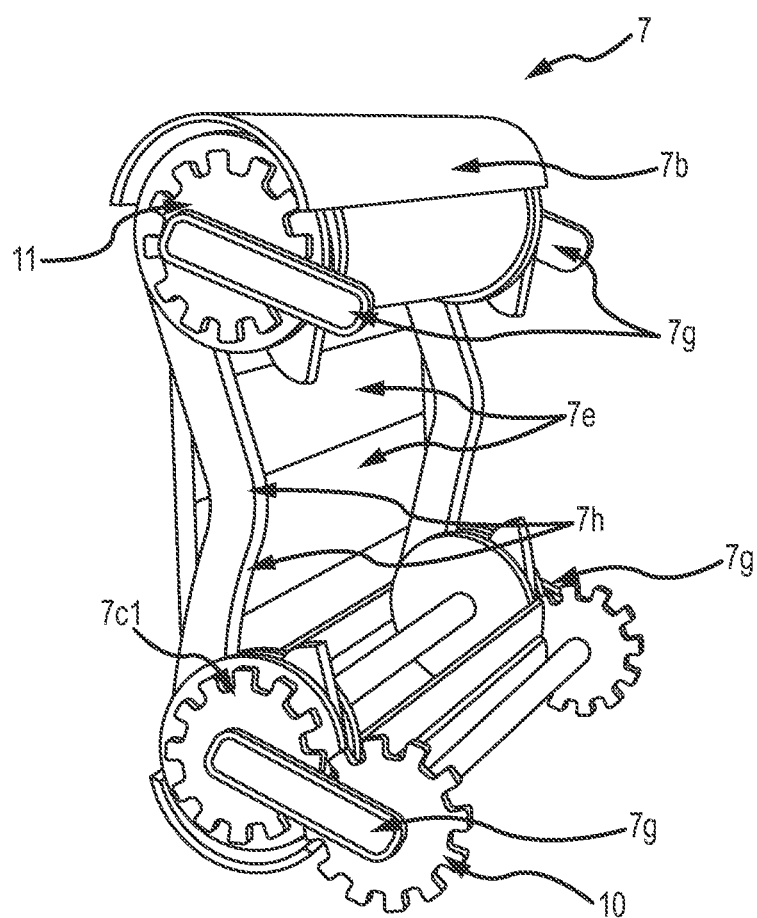
FIG. 3E is a partial rear left perspective view of components of the embodiment of a cleaning device of FIG. 3A.

To assist in the understanding of the present invention the following list of components and associated numbering found in the drawings is provided herein:

| # | Component |
|---|---|
| 1 | Pull Lever |
| 2 | Push Button |
| 3 | Disinfecting Surface |
| 4 | Front Cover |
| 4a | Opening to Disinfecting Surface (aka Aperture) |
| 4b | Front Cover Latch |
| 4c | Front Cover Hinges (not shown) |
| 5 | Main Housing (aka Housing) |
| 5a | Back Plate |
| 5b | Back Plate Screw Holes |
| 5c | Receiving Sliding Tracks |
| 6 | Disinfecting Towelettes Dispenser |
| 7 | Replaceable Disinfecting Cartridge (aka Wipe Device) |
| 7a | Fresh Disinfecting Wipe Winding Axis |
| 7b | Fresh Disinfecting Wipe Protective Cover |
| 7c | Used Disinfecting Wipe Winding Axis |
| 7c1 | Winding Cogwheels |
| 7d | Used Disinfecting Wipe Protective Cover |
| 7e | Hard Surface Support |
| 7f | Currently Used Disinfecting Wipe |
| 7g | Sliding Inserts |
| 7h | Replaceable Cartridge Structural Connector |
| 8 | Disinfecting Towelette bay |
| 8a | Disposable Towelette Tub |
| 9 | Electric Motor |
| 10 | Activating Cogwheels |
| 11 | Activating Axis |
| 20 | Cleaning Device |

DETAILED DESCRIPTION OF EMBODIMENTS

The following detailed description illustrates the invention by way of example and not by way of limitation. This description will clearly enable one skilled in the art to make and use the invention.

To reduce the need to provide extensive disclosure in this application, but to provide adequate written description of the various devices and methods encompassed by the numerous embodiments of the present invention, the following patents are incorporated herein in their entireties by this reference: U.S. Pat. No. 7,503,335 to Perlman et al., U.S. Pat. No. 8,393,818 to Perlman et al., and U.S. Pat. No. 6,018,835 to Schonfeld. It will therefore be appreciated by one of skill in the art that various structural elements can be combined with the present structure of the present invention to achieve various desired purposes. For example, a housing may be used to isolate a means for cleaning, sterilizing or disinfecting a device from the surrounding environment, and ultraviolet light may be used to enhance the cleaning capacity of a cleaning device.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

An aspect of the present invention is a cleaning device, comprising a cleaning surface, further comprising a width and a length, a means for feeding the cleaning surface to a cleaning area, a means for receiving the cleaning surface from the cleaning area, a means for advancing the cleaning surface, and a signaling means. When a user activates the signaling means, the means for advancing moves a first portion of the cleaning surface from the means for feeding to the cleaning area and simultaneously moves a second portion of the cleaning surface from the cleaning area towards the means for receiving.

In some embodiments of the present invention, a cleaning surface may be constructed from a solid material comprising at least one plastic. As used herein, "plastic" refers to any of various organic compounds produced by polymerization, capable of being molded, extruded, cast into various shapes and films, or drawn into filaments used as textile fibers. A specified plastic can either be a thermosetting polymer or a thermoplastic polymer. Specifically, the plastic can include acetals, acrylics, acrylonitrile-butadiene-styrene, alkyds, cellulosics, coumarone-indene, diallyl phthalate, epoxy, fluoropolymer, melamine-formaldehyde, nitrile resins, nylon, petroleum resins, phenolics, polyamide-imide, polyarylates, polybutylene, polycarbonate, polyethylene, polyimides, polyphenylene oxide, polyphenylene sulfide, polypropylene, polystyrene, polyurethanes, polyvinyl acetate, styrene acrylonitrile, styrene butadiene latexes, sulfone polymers, thermoplastic polyester, unsaturated polyester, urea-formaldehyde, hexachloroethane, or any combination thereof. More specifically, the plastic can include polyethylene terephthalate (PET or PETE), high density polyethylene (HDPE), low density polyethylene (LDPE), polypropylene (PP), polystyrene (PS), nylon, or combinations thereof. The plastic can optionally include one or more additives.

In some embodiments of the present invention, the cleaning surface may be constructed from a paper material comprising at least one of a cellulose, hemicellulose, lignin and combinations thereof. In some further embodiments, the cleaning surface may be constructed of a naturally occurring material including, but not limited to, cellulose, animal hair, wool, silk, abaca coir, cotton, flax, jute, kapok, kenaf, raffia, bamboo, hemp, modal, ramie, sisal, glass, metals, plastic, and combinations thereof. In still further embodiments of the present invention, the cleaning surface may comprise a composite comprising at least one plastic and at least one paper material.

In some embodiments of the present invention the cleaning surface may comprise a bendable, flexible material, wherein the cleaning surface can be bent, twisted, or folded along any axis in three-dimensional space. The cleaning surface may comprise a substantially two-dimensional surface, plane or sheet. In some embodiments of the present invention, the cleaning surface may comprise a thickness ranging from about 0.5 mm to about 2.0 cm. In still further embodiments of the present invention, the cleaning surface is at least somewhat compressible along the axis corresponding to the thickness of the cleaning surface. In some embodiments, the cleaning surface is compressible to from about 98% to about 20% of the uncompressed thickness of the cleaning surface. The cleaning surface may be compressible to facilitate better contacting of the cleaning surface with irregularly shaped surfaces to be cleaned; e.g. surfaces other than perfectly flat surfaces such as the diaphragm of a stethoscope. A compressible cleaning surface may provide a moldable cleaning surface that naturally conforms to the shape of medical device being cleaned when the user presses the medical device against the cleaning surface.

In some embodiments of the present invention, the cleaning surface that contacts the medical device to be cleaned may comprise a surface structured to provide improved mechanical cleaning properties. As used herein, "mechanical cleaning properties" refers to the use of mechanical friction to remove or dislodge an undesirable contaminating layer, film, deposit, coating, covering or skin from the surface of a medical device. This is typically accomplished by moving a cleaning surface in at least one direction relative to the surface to be cleaned; e.g. the head of a stethoscope. For example, the mechanical cleaning properties of the cleaning surface may be enhanced by incorporating ribs, cord or veins that cross the width of the cleaning surface and provide a raised or elevated surface relative to the thickness of the non-ribbed cleaning surface. Such ribs may be perpendicular to the longitudinal axis of the clean surface. Alternatively, the ribs incorporated into the cleaning surface may pass diagonally across the cleaning surface. In still further embodiments of the present invention, the mechanical cleaning properties of the cleaning surface may be enhanced by using two sets of diagonal ribs, wherein the first set are placed diagonally across the cleaning sheet and rise from left to right, wherein the second set are placed diagonally across the cleaning sheet and rise from right to left, wherein the two sets of ribs intersect one another to create a diamond pattern of ribs on the cleaning surface.

In some embodiments of the present invention, the mechanical cleaning properties of the cleaning surface may be enhanced by incorporating a low abrasive or low hardness material into or onto the cleaning surface. In some embodiments of the present invention, the material may comprise a powder, granule or fiber. In some embodiments, a low abrasive material comprises a hardness of less than 6 Mohs. In some embodiments, a low abrasive material comprises a material that is less abrasive than pumice. In some further embodiments, an abrasive material may be utilized to enhance the mechanical cleaning properties of the cleaning surface. In some embodiments, an abrasive material comprises a hardness of more than 6 Mohs. In some further embodiments of the present invention, an additive may be added to the cleaning surface to increase the mechanical cleaning properties of the cleaning surface wherein the additive is selected from the group consisting of an alumina, a silicon carbide, an iron oxide, graphite, steel, glass, an organic, and combinations thereof.

In some embodiments of the present invention, the additive for improving the mechanical properties of the cleaning surface may be added only to the outer layer of the cleaning surface that is in direct contact with the medical device to be cleaned. In other embodiments, the additive for improving the mechanical properties of the cleaning surface may be incorporated throughout the mass of the cleaning surface; e.g. throughout the entire thickness of the cleaning surface. In some further embodiments of the present invention, the additive for improving the mechanical properties of the cleaning surface is added on a mass basis from greater than about 0 wt % to about 80 wt %. In still further embodiments of the present invention, the additive for improving the mechanical properties of the cleaning surface is added on a mass basis from greater than about 0 wt % to about 10 wt %.

In some embodiments of the present invention, the additive for improving the mechanical properties of the cleaning surface may be a fiber. The fiber may be a naturally occurring fiber or a synthetic fiber. A fiber used as an additive for improving the mechanical properties of the cleaning surface may be an animal-based fiber, a plant-based fiber, a mineral-based fiber, a synthetic fiber, and combinations thereof. A fiber additive for improving the mechanical properties of the cleaning surface may be selected from the group consisting of cellulose, animal hair, wool, silk, abaca coir, cotton, flax, jute, kapok, kenaf, raffia, bamboo, hemp, modal, ramie, sisal, glass, metals, plastic, and combinations thereof.

In some embodiments of the present invention, the cleaning surface may possess absorbency for a liquid additive. Absorbency may be quantified in various ways, known to one of ordinary skill in the art. By way of example only, the absorbency of a liquid additive into the cleaning surface may be quantified by the mass of liquid taken up per unit surface area of the "dry" cleaning surface. Alternatively, the absorbency may be quantified by the mass of liquid additive absorbed per unit mass of the "dry" cleaning surface. In some embodiments of the present invention, the absorbency of the cleaning surface may range from about zero grams of liquid additive per gram of dry cleaning surface, to about 10 grams of liquid additive per gram of dry cleaning surface. In further embodiments of the present invention, the absorbency of the cleaning surface may range from about zero grams of liquid additive per gram of dry cleaning surface, to about 1.0 gram of liquid additive per gram of dry cleaning surface.

In some embodiments of the present invention, the cleaning surface provides both a mechanical cleaning mechanism and a chemical cleaning mechanism. In some further embodiments, the cleaning surface itself provides at least one of a mechanical cleaning mechanism and a chemical cleaning mechanism. In still further embodiments, the cleaning surface provides at least one of a mechanical cleaning mechanism and a chemical cleaning mechanism and also acts as a carrier for transporting at least one additive that provides a mechanical cleaning mechanism, a chemical cleaning mechanism, or both. In still further embodiments, the cleaning surface acts as a carrier for transporting at least one additive that provides a mechanical cleaning mechanism, a chemical cleaning mechanism, or both.

In some embodiments of the present invention, an additive comprising a chemical cleaning mechanism is selected from the group consisting of a phenolic, a quaternary ammonium compound, an alcohol, a hypochlorite, iodine, an iodophor, hydrogen peroxide, gluteraldehyde, formaldehyde, ortho-phthalaldehyde, peracetic acid, and combinations thereof. Still further examples of additives comprising a chemical cleaning mechanism include, but are not limited to, sodium hypochlorite, dilute bleach, ethanol, isopropanol, potassium permanganate, potassium peroxymonosulfate, phenolics, silver, copper, and combinations thereof. An additive comprising a chemical cleaning mechanism may be a solid, a liquid, a gas, and combinations thereof.

In still further embodiments of the present invention, the cleaning surface may comprise sodium hypochlorite. In still further embodiments of the present invention, the cleaning surface may comprise isopropanol, benzyl-C12-18-alkyldimethyl ammonium chloride, and quaternary ammonium compounds. In still further embodiments of the present invention, the cleaning surface may comprise isopropanol, ethylene glycol monobutyl ether, diisobutylphenoxyethoxydimethylbenzyl ammonium chloride, and water. In still further embodiments of the present invention, the cleaning surface may comprise trisodium phosphate dodecahydrate, and sodium hypochlorite. In still further embodiments of the present invention, the cleaning surface may comprise benzyl-C12-18-alkyldimethyl ammonium chloride, and quaternary ammonium compounds. In still further embodiments of the present invention, the cleaning surface may comprise 2-propanol, 2-butoxy-ethanol, benzyl-C12-18-alkyldimethyl ammonium chloride, and quaternary ammonium compounds.

In some embodiments of the present invention, the cleaning surface may be defined by a width ranging from about the width of a stethoscope head to about the width of an average hand. In still further embodiments, the cleaning surface may be defined by a width ranging up to the average width two hands pushing on the surface perpendicularly with a comfortable distance in between hands allowing all 10 fingers to be comfortably spread. In still further embodiments of the present invention, the cleaning surface may be defined by a width ranging from about 3.0 cm to about 50.0 cm. In still further embodiments of the present invention, the cleaning surface may be defined by a width ranging from about 3.0 cm to about 100.0 cm.

In some embodiments of the present invention, the cleaning surface may comprise a laminated construction comprising at least two layers, wherein the widths and lengths of the two layers are substantially the same. In some embodiments a cleaning surface may comprise a laminated construction comprising at least two layers, wherein the at least two layers are attached. The at least two layers of a laminated construction may be attached by any suitable means. Examples include, but are not limited to, mechanically attaching the at least two layers using staples or by stitching using thread, string, fiber, etc., or by adhering the at least two layers utilizing a glue or adhesive. Alternatively, the at least two layers of a cleaning surface comprising a laminated construction may be attached by using a first layer comprising a thermosetting plastic material, whereby the plastic is temporarily softened by heating it above its softening point, promoting the adhesion of the first plastic material to the at least one remaining layer. Subsequent cooling will result in the hardening of the thermosetting plastic, resulting in a permanent bond with the at least one remaining layer.

In some embodiments of the present invention a cleaning surface comprising a laminated construction comprising at least two layers, wherein a first layer provides mechanical support and stability, and at least one remaining layer provides at least one of a mechanical cleaning mechanism, a chemical cleaning mechanism, a compressible surface, and combinations thereof. In some embodiments, a cleaning surface comprising a laminated construction comprises at least two layers, wherein a first layer provides mechanical support and stability, and at least one remaining layer provides at a mechanical cleaning mechanism, a chemical cleaning mechanism, and is compressible, wherein the compressible layer can be compressed to range from about 98% to about 10% of the compressible layer's uncompressed thickness.

In some embodiments of the present invention, the cleaning surface may be defined by a length ranging from about 10 meters to about 1000 meters. In still further embodiments of the present invention, the cleaning surface may be defined by a length ranging from about 10 meters to about 200 meters. In still further embodiments of the present invention, the cleaning surface may be defined by a length ranging from about 10 meters to about 100 meters.

In one embodiment, the cleaning surface is provided as a commercially-available product, such as a rolled product comprising a plurality of cleaning wipes and/or cleaning surfaces.

In some embodiments of the present invention, the cleaning surface may be located in or on a means for feeding. In some embodiments of the present invention, a means for feeding comprises a feed enclosure, housing, or cartridge, wherein substantially the entire length and width of the cleaning surface is initially located within the enclosure, housing, or cartridge. In some further embodiments of the present invention, at least a portion of the cleaning surface may be located within a feed housing to form a disposable and removable cleaning surface system. Therefore, the scope of the present invention includes a medical device cleaning apparatus or system, comprising integral components, wherein one of the components is an easily removable, disposable, reusable, recyclable and/or refillable cartridge system or unit that provides a defined amount of cleaning surface to be used in the medical device cleaning apparatus or system. Such a feed housing may further comprise a first axis around which is initially wound a substantial portion or the entire length of the cleaning surface. The feed housing itself may be cylindrical in shape, or any other suitable shape, further comprising an opening, hole, slot, or slit to allow the cleaning surface to be fed out of the feed housing to a target destination for use in cleaning a medical device. In such embodiments, the cartridge containing the cleaning surface may be loaded into the medical device cleaning apparatus or system via any suitable means. For example, receiving slots may mechanically connect with the opposing ends of the first axis. Alternatively, a retractable pin system, or any other suitable connecting means, may be used to connect the feed housing containing the cleaning surface to the medical device cleaning apparatus or system Alternatively, the cleaning surface may be wound around a first axis and subsequently packaged in a suitable packaging material (e.g. plastic or foil), wherein the cleaning surface is subsequently removed from the packaging when needed in the care-giver's environment (e.g. in the examining room) and mounted in a feed housing that is permanently or removably affixed and/or integrally a part of the medical device cleaning apparatus or system.

In some embodiments of the present invention the means for feeding the cleaning surface has a corresponding means for receiving the cleaning surface. The means for feeding stores and provides the clean, unused cleaning surface. The means for receiving receives and stores dirty, contaminated, and/or used cleaning surface for eventual disposal or recycling, thereby preventing the user from ever directly touching the contaminated wipe surface.

In some embodiments of the present invention, a means for receiving comprises a receiving enclosure, housing, or cartridge, wherein substantially the entire length and width of the used cleaning surface is finally located within the receiving enclosure, housing, or cartridge. At this point in time, most or all of the unused cleaning surface has been transferred out of the feeding means, has been used by the care-giver to clean medical devices or otherwise, and the resultant used, dirty cleaning surface has been transferred to the receiving means. In some further embodiments of the present invention, at least a portion of the used cleaning surface may eventually be located within the receiving housing to form a disposable and removable used cleaning surface system, also referred to as a "wipe device." The scope of the present invention comprises a medical device cleaning apparatus or system, comprising integral components, wherein one of the components is an easily removable, disposable, reusable, recyclable and/or refillable receiving cartridge system or unit that provides a useful storage system for collecting and removing a defined amount of used cleaning surface that has been utilized for cleaning devices in the medical device cleaning apparatus or system. Such a receiving housing may further comprise a second axis around which is finally wound a substantial portion or the entire length of the used cleaning surface. The housing itself may be cylindrical in shape, or any other suitable shape, further comprising an opening, hole, slot, or slit to allow the used cleaning surface to enter the receiving housing after being used for cleaning in the cleaning a medical device. In such embodiments, an empty receiving cartridge may be loaded into the medical device cleaning apparatus or system via any suitable means, and subsequently removed once at its carrying capacity for used cleaning surface has been reached. For example, receiving slots may mechanically connect with the opposing ends of the second axis of the receiving cartridge. Alternatively, a retractable pin system, or any other suitable connecting means, may be used to connect the receiving cartridge housing to the medical device cleaning apparatus or system Alternatively, the used cleaning surface may be progressively wound around a second axis, as the cleaning surface is used, wherein the used cleaning surface is subsequently removed from the medical device cleaning apparatus by removing the second axis. The used cleaning surface and its carrying second axis may then be disposed of, recycled, etc. Alternatively, the used cleaning surface may be unwound from the second axis by any suitable means, after which the cleaning surface is disposed of or recycled, and the second axis is reused in the medical device cleaning apparatus. An intermediate step may include disinfecting or sterilizing the second axis before reuse.

In some embodiments of the present invention, the means for advancing the cleaning surface may comprise a motor. In some preferred embodiments, the means for advancing may comprise an electric motor. The electric motor may be powered utilizing a standard 110 volt power supply, e.g. from a standard electrical socket, or alternatively, the electric motor may be battery operated. In still further embodiments of the present invention the means for advancing comprises an electric motor mechanically connected to at least one of the feeding means and receiving means. In still further embodiments of the present invention, an electric motor drives the rotation of at least one of the first axis and the second axis, whereby in the exemplary case of continuous rotation of the at least one of the first axis and the second axis, advances the cleaning surface from the feed housing, through a target destination for use in cleaning a device, to a collection of the used cleaning surface in the receiving housing, until the entire length of the cleaning surface has been transferred from the first axis in the feed housing, to the second axis in the receiving housing.

In some further embodiments of the present invention, the means for advancing may comprise a lever, wherein a first end of the lever is in mechanical communication with at least one of the means for feeding and means for receiving, such that pulling a second end of the lever causes the first end of the lever to induce rotation of at least one of the first axis and the second axis. In still further embodiments, when a care-giver wishes to clean a medical device, which begins with advancing a clean and unused portion of the cleaning surface to a target area for cleaning, the care-giver activates the transport of clean, unused cleaning surface by gripping the second end of a lever, and pulling on the second end of the lever. Because the first end of the lever is mechanically connected to the second axis of the receiving means, the second axis is rotated a fixed number of degrees corresponding to the arc of rotation of the lever. Because the leading edge of the cleaning surface is mechanically attached to the second axis, rotation of the second axis pulls a portion of the cleaning surface onto the second axis.

In some embodiments of the present invention, a signaling means triggers the advancement of the cleaning surface from the feeding means, to a target area for use, and subsequently to the receiving means for storage and eventual disposal. In some embodiments, pressing a button or switch applies power to an electrical motor, which when powered on, causes rotation of at least one of the first axis and the second axis. In still further embodiments, when a care-giver wishes to clean a medical device, the care-giver activates the transport of clean, unused cleaning surface by pressing the button or switch, thereby turning on the electric motor, which in turn rotates the second axis of the receiving means. Because the leading edge of the cleaning surface is mechanically attached to the second axis, rotation of the second axis pulls a portion of the cleaning surface onto the second axis.

In still further embodiments of the present invention, a signaling means may comprise a button, switch, pressure transducer, or other similar means, wherein the signaling means is located on the opposite side of the cleaning surface that is in physical contact with the medical device being cleaned. In some embodiments of the present invention, the signaling means is located by the cleaning surface. In this exemplary arrangement, application of the medical device to the cleaning surface results in the button, switch, or pressure transducer being activated, causing the electrical motor to turn on and rotate the second axis of the receiving means, ultimately advancing a portion of the cleaning surface from the feeding means towards the receiving means. In some cases, the motor may remain activated the entire duration of time that the button, switch, or pressure transducer is depressed or activated. In other cases, the motor may only turn on for a predefined period of time for each instance that the button, switch, or pressure transducer is initially activated. Such a system has the added potential benefit of being "hands-free" and potentially gives the care-giver the option of using one hand for other activities, while using his/her first hand to apply the medical device to the device cleaning apparatus.

In still further embodiments of the present invention, a signaling means may comprise a motion sensing device that senses the presence of a medical device, and activates an electric motor when the medical device is substantially near to the cleaning surface, and subsequently turns the electric motor off when the medical device is not within a predefined proximity of the cleaning surface. A motion sensing device may comprise any standard available motion sensor known to one of ordinary skill in the art; e.g. optical, infrared, ultrasound, microwave, tomographic, etc. A motion sensing system also has the added potential benefit of being "hands-free." In one embodiment, an indicator is provided, such as a colored light, to indict the state of the cleaning device. For example, a red light might indicate that the device is not ready for use (e.g. an unclean wipe is presented to the user), and a green light to indicate the device is ready to use, e.g. to indicate a sterile or unused wipe is presented to the user to employ to clean a medical device. A yellow light might indicate a transitional stage, e.g. when a used wipe is moving toward a receiving roller and an unused or sterile wipe is moving away from (unwinding from) an output roller so as to be positioned for use.

In some embodiments of the present invention, the cleaning area may comprise a clean, unused portion of the cleaning surface that is accessible to the user for cleaning a medical device In other words, the cleaning area may comprise a portion of the cleaning surface that is neither in a housing for the means for feeding or in a housing for the means for receiving the cleaning surface. As one of ordinary skill in the art would recognize, providing a cleaning area of sufficient size for cleaning requires both a width and a length of the cleaning area. In some embodiments of the present invention, the width of the cleaning area may be substantially equal to the width of the cleaning surface. In still further embodiments, the width of the cleaning area may be less than the width of the cleaning surface. In some embodiments of the present invention, the length of the cleaning area may be defined by a distance separating the means for feeding from the means for receiving. In some cases, the length of the cleaning area may be substantially equal to the distance separating the means for feeding from the means for receiving. In still further embodiments, the length of the cleaning area may be less than the distance separating the means for feeding from the means for receiving. One should understand that the cleaning area is not necessarily restricted to rectangular or square shapes. Any other suitable shaped cleaning area falls within the scope of the present invention, including, but not limited to, circular, elliptical, oval, and any other suitable shape.

In some embodiments of the present invention, the cleaning area may comprise a characteristic width ranging from about 4 cm to about 50 cm. In still further embodiments, the cleaning area may comprise a characteristic width ranging from about 4 cm to about 20 cm. In still further embodiments, the cleaning area may comprise a characteristic width of less than 4 cm. In some embodiments of the present invention, the cleaning area may comprise a characteristic length ranging from about 4 cm to about 50 cm. In still further embodiments, the cleaning area may comprise a characteristic length ranging from about 4 cm to about 20 cm. In still further embodiments, the cleaning area may comprise a characteristic length of less than 4 cm.

In some embodiments of the present invention, a cleaning device or apparatus may further comprise a structural support that connects the means for feeding to the means for receiving. For example, a structural support may comprise a planar structure positioned vertically and comprising a top end and a bottom end, wherein the means for feeding is attached to the top end, and the means for receiving is attached to the bottom end. In some embodiments, where the means for feeding comprises a housing containing a first axis with the cleaning surface wound thereon, a portion of an outer surface of the feed housing may be attached to the top end of the structural support, wherein the first axis is horizontally oriented and positioned across the vertical axis of the structural support. Similarly, for an embodiment where the means for receiving comprises a housing containing a second axis with the used cleaning surface wound thereon, a portion of an outer surface of the receiving housing may be attached to the bottom end of the structural support, wherein the second axis is horizontally oriented and positioned across the vertical axis of the structural support. In some embodiments of the present invention, the first axis and second axis are parallel, and the distance between the first axis and the second axis, and the width of the cleaning surface defines the size of the cleaning area.

As one of ordinary skill in the art would appreciate, the width and thickness of the structural support can be of any suitable dimensions so as to provide the mechanical strength and durability needed for the device cleaning apparatus withstand the forces generated during normal use.

In still further embodiments, a structural support may include a track or rail upon a surface of the structural support, to which at least one of the means for feeding and the means for receiving is slideably engaged. In some embodiments, at least one of the means for feeding and the means for receiving may further comprise a locking mechanism, whereby the user can adjust the size of the cleaning area, by changing the distance between the means for feeding and the means for receiving, by releasing the locking mechanism of at least one of the means for feeding and the means for receiving, sliding one or both vertically along the track to a desired position or separating distance, and locking this position in place by relocking the locking mechanism.

In some embodiments, a structural support may also provide a surface for attaching the device cleaning apparatus to a wall or other desired location.

In some embodiments of the present invention, a structural support may be positioned behind a portion of the cleaning surface in the cleaning area, wherein the structural support and the portion of the cleaning surface are in substantially parallel planes, and wherein the structural support provides resistance to forces applied by the user when the user presses an object against the portion of the cleaning surface in a direction substantially perpendicular to the cleaning surface. In other words, in some embodiments the structural support not only provides a means for attaching the means for feeding and the means for receiving the cleaning surface, but also provides a mechanical "backstop" that prevents the cleaning surface from ripping or tearing when the care-giver presses the device to be cleaned, e.g. stethoscope, against the cleaning surface in the cleaning area. Some embodiment are envisioned, wherein the means for feeding and means for receiving are attached to opposite ends of a telescoping structural support, whereby the user can adjust the length of structural support as needed to create a cleaning area of a desired size and length.

In some embodiments of the present invention, the device cleaning apparatus may further comprise a support surface positioned behind a portion of the cleaning surface in the cleaning area, wherein the support surface and the portion of the cleaning surface are in substantially parallel planes, and wherein the support surface provides resistance to forces applied by the user when the user presses an object against the portion of the cleaning surface in a direction substantially perpendicular to the cleaning surface. In some embodiments of the present invention, a support surface may be mounted to a support structure or to any other suitable mechanical component of the device cleaning apparatus. In some embodiments of the present invention, the support surface may comprise a means for compressing. The means for compressing may provide a moldable "back stop" that naturally conforms to the shape of medical device being cleaned when the user presses the medical device against the cleaning surface. It is envisioned that such a moldable embodiment of the present invention may be utilized to clean a person's hand or hands, in addition to being capable of cleaning a device or devices. A partially moldable or moldable back stop behind the cleaning surface would somewhat conform to the shape of the object being cleaned, also providing a bit of a lateral force when the disinfecting wipe slides over it, that way cleaning around the edges (or in case of a hand pressed against the cleaning surface—in between the fingers). Alternatively, the support surface may further a spring or piston that allows some movement of the support surface in reaction to the user applying a normal force against the cleaning surface.

In one embodiment, the support surface does not remain fixed in position from an initial (non-use) position to a more distal (relative to the aperture) position when the medical device to be cleaned is in contact with the wipe so as to be cleaned or while being cleaned. Stated another way, the support surface operates in at least two states or positions: a first position (a nominal position when the cleaning device is not in use) and a second position when the cleaning device is in use. In another embodiment, the support surface is not parallel to the aperture of the housing of the medical device when a medical device (such as a stethoscope) is engaged with a cleaning wipe and/or the medical device is being cleaned.

In some further embodiments of the present invention, the medical device cleaning apparatus further comprises a means for traction, wherein the means for traction provides a force that opposes the movement of the cleaning surface from the feeding means towards the receiving means. For example, in the case were the means for feeding comprises a first axis mounted in a housing, upon which the cleaning surface is wound, and the means for receiving comprises a second axis, also mounted in a housing, wherein the axes are parallel to one another, with the cleaning surface spanning a length therebetween, a traction device may apply a force substantially parallel to the length of the cleaning surface. A traction device will insure that there is no "slack" in the cleaning surface when being used and/or when adjusting the length between the means for feeding and the means for receiving. A means for traction may comprise a spring assembly attached to the first axis of the means for feeding, or any other suitable force generating apparatus.

As one skilled in the art will understand, the materials of construction used to build any of the embodiments of the present invention, and elements thereof, will be selected based on the ultimate use and location of an individual embodiment, as well as based on manufacturing and maintenance costs. However, examples of materials of construction include any suitable material, including metals, plastics, glass, ceramics, and combinations thereof.

A further aspect of the present invention is a method for cleaning a medical device and/or a care-giver's hands, the method comprising storing a cleaning surface in a suitable storage means, providing a portion of the cleaning surface to the care-giver such that the care-giver contacts at least one object with the cleaning surface such that the object is cleaned, disinfected and/or sterilized, and receiving a used, dirty portion of the cleaning surface in a means for receiving.

All publications, patents, and patent documents cited herein are incorporated by reference herein, as though individually incorporated by reference. The invention has been described with reference to various specific and preferred embodiments and techniques. However, it should be understood that many variations and modifications may be made while remaining within the spirit and scope of the invention.

It is appreciated that certain features of the invention, which are, for clarity, described in the context of separate embodiments, may also be provided in combination in a single embodiment. Conversely, various features of the invention that are, for brevity, described in the context of a single embodiment, may also be provided separately or in any sub-combination.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

Referring now to FIGS. 1-4, a particular embodiment of the cleaning device 20 is presented. Generally, the cleaning device 20 comprises a main housing 5 with aperture 4a (aka opening to disinfecting surface) and a wipe device 7 (aka replaceable disinfecting cartridge). The wipe device 7 advances a new and sterile disinfecting wipe near or behind the aperture, the wipes advancing by way of a pair of rollers. The user positions the medical device to be cleaned against the sterile wipe 7f. The action of the wipe moving against the medical device to be cleaned, either by action of the rollers moving the wipes against the to-be-cleaned device and/or by the user pressing and/or rubbing the medical device against the wipe 7f, serves to clean the medical device. The now-used wipe 7f is advanced from a first roller to a second roller, thereby presenting a fresh, and sterile, wipe at the aperture 4a for a next cleaning. Disposed behind or distal to the wipe 7f is a hard surface support 7e (aka surface support) which engages the wipe 7f when the user presses a medical device for cleaning against the wipe 7f.

In some embodiments the hard surface support 7e is not parallel to a plane formed by the aperture 4a. In some embodiments the hard surface support 7e is substantially parallel to a plane formed by the aperture 4a. In some embodiments the hard surface support 7e forms at least two surfaces with a discontinuity between surfaces, e.g. forming a V shape when viewed in cross-section (See e.g. FIG. 3B).

The cleaning device 20 may be installed right outside of or inside each patient room for easy convenient access, not unlike the currently available hand sanitizers. The entire unit is mounted directly on the wall, via back plate screw holes 5b on the back plate 5a of the main housing 5. Upon entering a room, a health care worker would utilize the disinfecting surface 3 to clean, disinfect, and or sterilize the medical device of choice, e.g. a stethoscope diaphragm, or a care-giver's hands. The cleaning surface 3 is the outside surface wipe 7f of a replaceable disinfecting cartridge 7. The replaceable disinfecting cartridge 7 is exposed to the user in the aperture 4a to disinfecting surface i.e. cleaning wipe 7f, through the opening or aperture 4a on the front cover of housing 5, which allows access to the disinfecting surface 3.

The replaceable disinfecting cartridge 7 comprises the disinfecting surface 3 made up of a series of interconnected disinfecting wipes that are wound onto the two winding axes, first axis 7a and second axis 7c, into cylinder forms which are enclosed by protective covers or housings 7b and 7d. The disinfecting surface 3, in this case the series of wipes, is exposed at location 7f in the cleaning area and kept tightly flat in the cleaning area aperture 4a; the back of this surface is supported by a hard surface support 7e which prevents the wipe from collapsing when a stethoscope diaphragm is pushed onto the disinfecting surface in the cleaning area 4a. In an alternate embodiment, the hard surface support 7e, while held flat, presents a surface that is not parallel to the aperture 4a.

The medical device cleaning apparatus 20 is operated by placing a stethoscope diaphragm against the disinfecting surface 3 and then advancing the disinfecting wipe by a pull lever 1 and/or a push button 2 by pushing on a push button 2, which in turn activates an electric motor 9. Either mechanism works by directly turning the activating cogwheels 10, which are connected by activating axis 11 and are connected with the main housing 5. The activating cogwheels 10 subsequently turn the winding cogwheels 7c1 of the used disinfecting wipe winding axis 7c. The first and second mechanical means are designed such that one "pull" of the pull lever 1 or "push" of the push button 2 advances the portion of the currently used disinfecting wipe 7f one entire length of a disinfecting wipe of the disinfecting surface 3 and winds it onto the used disinfecting wipe winding axis 7c for collecting and storing used, now non-sterile portions of the cleaning surface. This movement allows a fresh disinfecting wipe to be dragged over the stethoscope diaphragm surface, therefore providing a cleaning action in such a way so that the user does not have to touch the disinfecting wipe directly. Stated another way, the movement of the disinfecting wipe over the device to be cleaned is the means of cleaning the medical device. In contrast, conventional cleaning systems present a cleaning surface and task the user to rub or perform cleaning himself. While the user may still perform such additional rubbing on the presented cleaning surface, the movement of the cleaning wipe by the device 20 provides substantial if not the principal means to clean the medical device.

In one embodiment, the aperture 4a is covered by a cover when not in use, the cover configured to move to provide access to the aperture 4a when a user engages the device 20.

In the replaceable cartridge embodiment of the replaceable disinfecting cartridge 7, the cartridge will come airsealed in order to protect the freshness of the disinfecting wipe, which is saturated with the industry standard disinfecting chemicals. Once removed from the protective package, a new replaceable cartridge is inserted into the main housing 5 in the following manner: a front cover 4 is locked in by the front cover latch 4b, e.g. latches, which are unlatched, and the front cover 4 is opened by pulling out; it is secured to the main housing 5 by the front cover hinges (not shown) 4c. The replaceable disinfecting cartridge 7 is then inserted so that the sliding inserts 7g on the cartridge slide into the receiving sliding tracks 5c on the main housing 5. (Note that in FIG. 3C, only one out of four receiving sliding tracks displayed for simplicity). This brings the first mechanical means comprising winding cogwheels 7c1 on the replaceable disinfecting cartridge 7 into the proximity of the second mechanical means comprising activating cogwheels 10 located in the main housing 5, so that the disinfecting wipe can be advanced as described above. See, e.g. FIG. 3 detailing the relationship of the replaceable disinfecting cartridge 7 to the main housing 5 and the cogwheels.

The cleaning device 20 may be used before and after each patient contact. The user would place the surface of their diaphragms onto the cleaning surface through the cleaning window, then pull the activating lever or push the button (depending on the product version) to advance the disinfecting wipe. The friction of the disinfecting wipe (which is also ribbed) against the diaphragm surface will provide mechanical force to remove common pathogens, including *Clostridium difficile* spores. In addition, the disinfecting chemicals will provide chemical sterilization, similar to using disinfecting wipes, except in a more convenient fashion, where the user will not have to directly touch the disinfecting chemicals with their own skin; the chemicals will evaporate between the disinfection and patient contact, therefore avoiding any possible chemical irritation to the patient's skin.

In another embodiment, the cleaning device 20 is activated by a sensor, e.g. a motion or proximity sensor. Here, when a user approaches the device 20 and/or places the surface of their stethoscope diaphragm onto the cleaning surface through the cleaning window, the disinfecting wipe is advanced and the medical device cleaned.

In another embodiment of the present invention, an optional feature is the ability to hold a disinfecting towelette tub 8a inside of the disinfecting towelette bay 8; the opening to this towelette tub serves at the dispenser for the disinfecting towelettes dispenser 6. This provides the user a convenient access to disinfecting wipes should they need to disinfect more than just the stethoscope diaphragm surface. The disinfecting towelette tub can be accessed and replaced by opening the front cover 4.

Furthermore, the wipe device 7 protects the user's skin from the potentially harmful or strong-odored disinfecting chemicals (such as sodium hypochlorite) found on a fresh disinfecting wipe. Of note, these chemicals rapidly evaporate from a hard surface such as a stethoscope diaphragm, and therefore do not pose a threat of irritating the patients' skin. Additionally, the convenience of having such an efficient disinfecting mechanism saves time and is likely to increase the compliance with routine stethoscope disinfection among health care workers.

Moreover, the disinfecting wipe is designed to have horizontal ribs (not shown) that can aid in mechanically removing *Clostridium difficile* spores from stethoscope diaphragm surfaces in addition to chemical disinfection.

Other embodiments of the present invention provide additional accessories and optional features, which are described below.

Main housing design variations. In order to support a wide variety of clients operating in different settings, the medical device cleaning apparatus will have alternative designs available to better suit the particular environment at stake. For example, designs such as a ladybug, flower, or a truck will be available for installation in health care institutions catering to children, in order to contribute to a theme-appropriate visual effect. On the other hand, in the health care settings where there is a potential for vandalism, such as correctional facilities or inner city emergency departments, the medical device cleaning apparatus will have an option of a metal housing to withstand mechanical force.

Advertising opportunities. Due to its unique position within patient rooms—whether hospital rooms or out-patient clinic exam rooms—embodiments of the present medical device cleaning apparatus have an opportunity to reach out to a variety of patients—aka potential customers—and deliver targeted advertising messages at a critical time. The front cover 4 of the main housing (see FIGS. 4A and 4B, part) can serve as an advertising surface where vendors would provide messages for a fee; alternatively, a battery powered mini flat screen can be placed on the cover, delivering audio-visual messages as well. The advertising could be tailored to the appropriate audience this way. For example, a cardiology office could display advertisements by a company manufacturing a new medication for treatment of high blood pressure or high cholesterol. On the other hand, there could be a system in place to tie a message's theme directly to a patient's hospital admission, so that the audio-visual advertisements automatically play based on the principal problem for hospitalization that is entered in the hospital's electronic medical record. This way, patients would be made aware of treatment options that are available for their particular condition, which would hopefully contribute to increase in their medication compliance and well being. By the same token, advertising companies would have an opportunity to reach a very specific and targeted audience at a critical time, when they are likely to make decisions to commit to a treatment of choice, provided by a particular company. The flat screen could also display barcode messages that patients could scan on their smart phones, in order to receive free samples, discounts, etc. As an example, imagine a patient with uncontrolled diabetes due to medication noncompliance, who is admitted to the hospital for a hyperglycemic crisis. The electronic advertising system that would be mounted onto the device cleaning apparatus would pull the principal problem form the electronic medical record, which would be "uncontrolled diabetes" or such. Then the system would automatically play audio-visual material displaying a new painless insulin pen, or a diabetes education class offered by a certain company. This particular patient would be at a critical point in their life when these messages would likely create a meaningful impact, and hopefully lead him or her to consider the options offered through the advertisements in order to improve their health. As mentioned above, the mini flat screen could display a bar code that this patient could scan and that way receive various free samples and discount, making it more likely for them to even consider the services offered by the advertisement. The potential financial benefit for the advertising companies would likely be significant as well. And because these targeted advertisements would come directly from the companies offering various services instead coming from the health care providers, there would be no conflict of interest on the part of the health care providers involved in caring for these patients. The same advertising companies could even offer to pay for replacement of the disposable cartridges so that there is no cost to the health care facility for using the present invention; this would not count as a gift, which is often times considered a conflict of interest, since legally the advertisement companies could own the medical device cleaning apparatus and just rent the space on the wall from health care facilities.

Compliance tracking system. Keeping its main goal in mind—that is, improving compliance with stethoscope disinfection and minimizing hospital-acquired infections—some embodiments of the present invention offer a convenient system for health care facilities to encourage and track its use. One feature envisioned and included in the scope of the present invention, is a small detection device that can attach to any stethoscope tubing, similar to a stethoscope name tag. It communicates wirelessly with the medical device cleaning apparatus units of the present invention, wherein each unit is equipped with wireless receivers. When a health care worker enters a patient's room equipped with the medical device cleaning apparatus and gets within a certain range of the unit, detection device can be programmed to beep to remind the healthcare worker to disinfect the stethoscope. When a detection device-equipped stethoscope is brought into a close proximity to the medical device cleaning apparatus, then the interaction will be registered as "confirmatory"; in other words, the health care worker will get credit for cleaning his/her stethoscope. On the other hand, if a health care worker is detected to have entered a room without cleaning his/her stethoscope, the interaction will be recorded as a "negative" and he or she will not receive credit. Such a tracking device would be issued to every employee of a hospital system whose job description would require them to use a stethoscope. There would be a central database of each user's compliance. Hospital systems could implement reward programs so that the most compliant employee receives a gift card every month for disinfecting their stethoscope routinely. This would serve to improve the overall disinfection compliance of a hospital system, and in turn decrease the rates of hospital-acquired infections.

Figure 6:
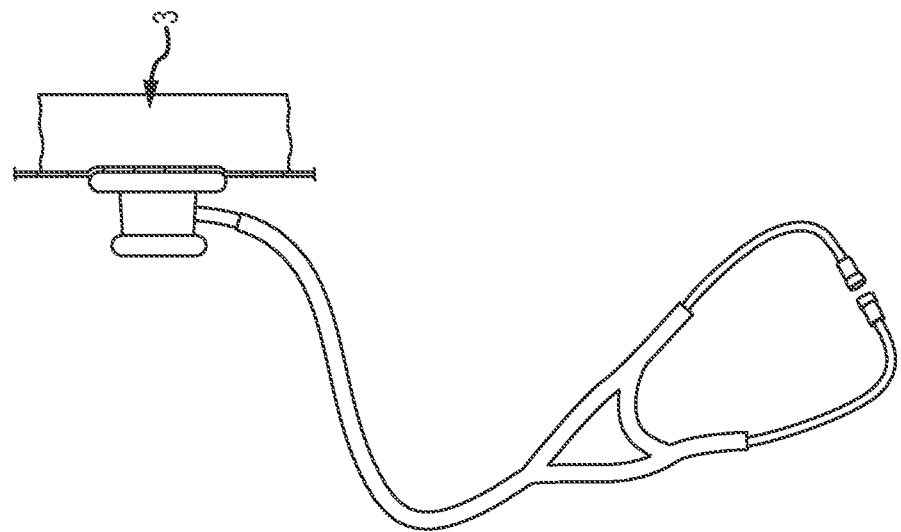
FIG. 6 depicts a right side plan view of a shape conforming disinfecting surface as engaged with a stethoscope.
Figure 5:
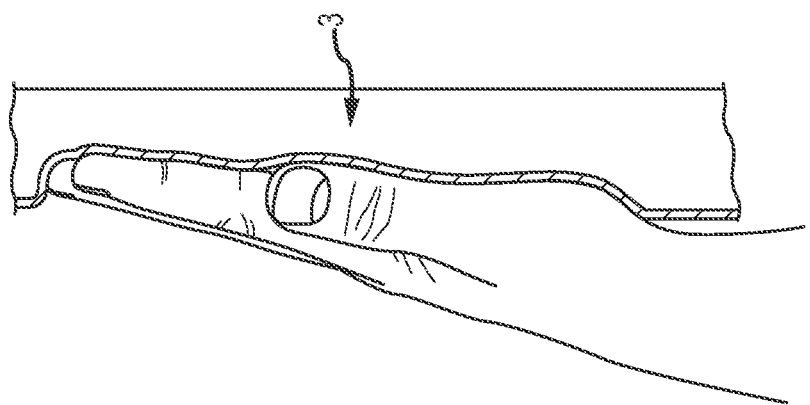
FIG. 5 depicts a right side plan view of a shape conforming disinfecting surface as engaged with a human hand.

Referring now to FIGS. 5 and 6, further embodiments of the present invention are illustrated. FIG. 5 illustrates a disinfecting surface 3 comprising a laminated construction, wherein a hand is shown in contact with a first layer that provides a mechanical and chemical means for cleaning the hand. The disinfecting surface 3 also comprises a second compressible layer that also provides mechanical stability to the first layer, and provides a compressible "back stop" that allows the disinfecting surface 3 to conform to the shape of the hand, thus providing more effective cleaning by accessing a larger percentage of the hands surface area.

Figure 7:
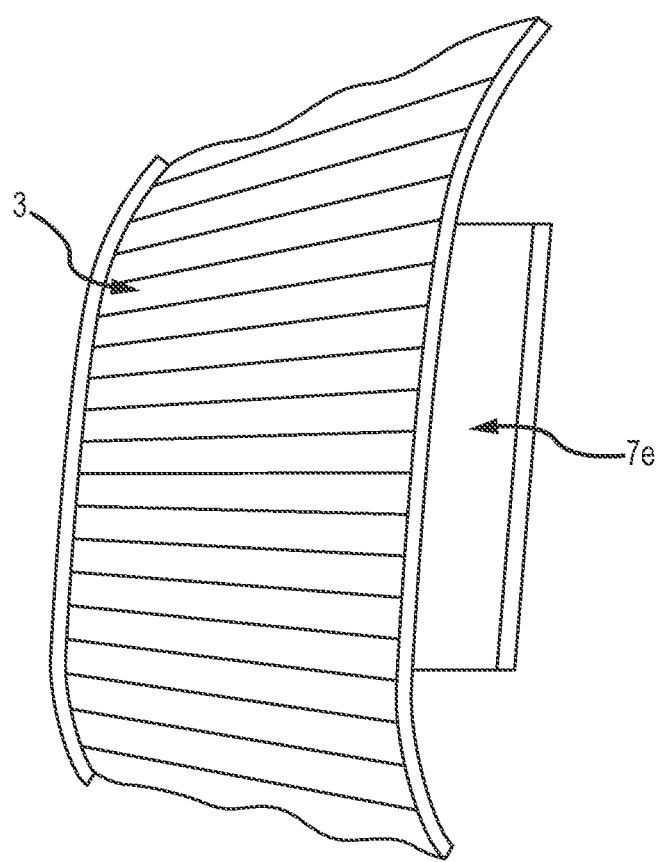
FIG. 7 depicts a disinfecting surface with a rigid backstop.

Referring now to FIG. 7, another embodiment of the present invention is illustrated, wherein the disinfecting surface 3 comprises a vertical ribbed structure to facilitate better mechanical cleaning of the medical device. Also shown, is one embodiment of a hard surface support 7e, which mechanical supports the disinfecting surface 3 and prevents it from ripping or tearing when the user pushes the device being cleaned against the disinfecting surface 3.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other structures, methods and systems for carrying out the several purposes of the present invention to create a garment comprising at least one pocket configured to carry, in a concealed and readily-accessible state, a handgun. It is important, therefore, that the claims be regarded as including any such equivalent construction insofar as they do not depart from the spirit and scope of the present invention.

What is claimed is:

1. A cleaning device to clean a medical device, the cleaning device comprising:
 a housing having a front cover with an aperture and defining an interior chamber configured to receive and secure a wipe device, the housing also having at least one activating cog rotatably interconnected to an inside surface of the housing;
 a wipe device comprising:
  a first roller comprised of a fresh disinfecting wipe winding axis with a sheet comprising a plurality of disinfecting wipes wrapped therearound,
  a second roller comprised of a used disinfecting wipe winding axis that secures a free end of the sheet, the second roller having a winding cog wheel operatively interconnected to the at least one activating cog, wherein rotation of the at least one activating cog rotates the second roller to move at least one disinfecting wipe from the first roller towards the second roller, and wherein used disinfecting wipes are maintained by the second roller and do not move towards the first roller; and
 a means for advancing associated with the activating cog and configured to selectively rotate the activating cog; and further comprising a disinfecting towelette tub integrated into the housing, the towelette tub having an opening that serves as a dispenser for disinfecting towelettes.

2. The cleaning device of claim 1, wherein the means for advancing is a lever that when pulled or pushed incrementally advances the sheet from the first roller toward the second roller.

3. The cleaning device of claim 1, wherein the first roller and the second roller are interconnected by at least one structural connector so that the first roller, the second roller, and at least one structural connector define a cartridge that is received within the housing, and further comprising a surface support interconnected to the at least one structural connector and located between the at least one structural connector and the sheet.

4. The cleaning device of claim 3, wherein the surface support is substantially not parallel to the aperture.

5. The cleaning device of claim 1, further comprising at least one track interconnected to an inner surface of the housing, and a sliding insert interconnected to at least one of the first roller and the second roller, the sliding insert adapted to be received within the at least one track to secure the wipe device within the housing.

6. The cleaning device of claim 1, wherein the plurality of disinfecting wipes comprise a laminated structure formed of a first layer configured to clean an item and a second layer that provides mechanical stability to the first layer.

7. The cleaning device of claim 1, wherein the plurality of disinfecting wipes have a ribbed structure.

8. The cleaning device of claim 1, wherein the means for advancing is a motor that incrementally advances the sheet from the first roller toward the second roller.

9. The cleaning device of claim 8, wherein the motor is activated when a button is pressed or when user proximity is sensed.

10. A cleaning device to clean a medical device, the cleaning device comprising:
a housing defining an interior chamber and configured to mount a wipe device, the housing comprising an aperture;
a disposable wipe device mounted within the interior chamber and comprising at least a first roller, a second roller, a surface support and a plurality of cleaning wipes, the plurality of cleaning wipes operatively engaged to the first roller and the second roller and configured only to travel from the first roller to the second roller;
a mechanism to advance the plurality of cleaning wipes, the mechanism configured to advance the plurality of cleaning wipes from the first roller to the second roller; and
wherein the plurality of cleaning wipes comprise a first cleaning wipe and a second cleaning wipe, wherein the mechanism to advance the plurality of cleaning wipes incrementally advances the first cleaning wipe from a position adjacent the aperture to a position toward the second roller and advances the second cleaning wipe to a position adjacent the aperture; and further comprising a disinfecting towelette tub integrated into the housing, the towelette tub having an opening that serves as a dispenser far disinfecting towelettes.

* * * * *